United States Patent [19]

Briody

[11] Patent Number: 4,650,916
[45] Date of Patent: Mar. 17, 1987

[54] REMOVAL OF MOLECULAR CHLORINE FROM 1,2-DICHLOROETHANE COMPOSITIONS CONTAMINATED WITH MOLECULAR CHLORINE

[75] Inventor: Robert G. Briody, Wadsworth, Ohio

[73] Assignee: PPG Industries, Inc., Pittsburgh, Pa.

[21] Appl. No.: 472,453

[22] Filed: Mar. 7, 1983

[51] Int. Cl.$^4$ ............................................. C07C 17/38
[52] U.S. Cl. .................... 570/252; 570/262; 570/254; 570/255
[58] Field of Search ................ 570/262, 252, 254, 255

[56] References Cited

U.S. PATENT DOCUMENTS

| | | | |
|---|---|---|---|
| 1,066,877 | 7/1913 | Best ................................... | 570/262 |
| 1,231,123 | 6/1917 | Brooks et al. . | |
| 2,043,932 | 6/1936 | Reynhart ........................... | 260/166 |
| 2,099,231 | 11/1937 | Ruys et al. ......................... | 260/162 |
| 2,245,776 | 6/1941 | Groll et al. ........................ | 260/662 |
| 2,356,785 | 8/1944 | Hammond ......................... | 202/42 |
| 2,393,367 | 1/1946 | Hammond ......................... | 260/660 |
| 2,601,322 | 6/1952 | Reese ................................. | 260/660 |
| 2,746,999 | 5/1956 | Gunkler et al. .................... | 570/246 |
| 3,470,260 | 9/1969 | Levine ............................... | 570/252 |

FOREIGN PATENT DOCUMENTS

| | | | |
|---|---|---|---|
| 462046 | 12/1949 | Canada ............................... | 570/254 |
| 2540257 | 4/1977 | Fed. Rep. of Germany ...... | 570/254 |

*Primary Examiner*—Natalie Trousof
*Assistant Examiner*—Joseph A. Boska
*Attorney, Agent, or Firm*—George D. Morris

[57] ABSTRACT

Olefins containing at least 7 carbon atoms are used to remove molecular chlorine form compositions comprising 1,2-dichloroethane and a contaminating amount of molecular chlorine.

18 Claims, No Drawings

REMOVAL OF MOLECULAR CHLORINE FROM 1,2-DICHLOROETHANE COMPOSITIONS CONTAMINATED WITH MOLECULAR CHLORINE

Compositions comprising 1,2-dichloroethane and a contaminating amount of molecular chlorine (other compounds are often also present) are typically introduced to equipment for storage, transportation and/or processing. Such equipment is susceptible to corrosion by or through the agency of molecular chlorine present unless it is constructed of specialized, corrosion-resistant materials. These materials are generally considerably more expensive than ordinary materials of construction, such as for example mild steel, and often they are exotic. Many of the corrosion-resistant materials are not totally resistant to corrosion, but are more resistant than ordinary materials of construction. In some cases, the rate of corrosion may be found unacceptably large only after the equipment has been constructed and operated for a period of time.

The mechanism of corrosion is unimportant so long as it is ultimately due to the presence of molecular chlorine in the composition. In some cases, the molecular chlorine may react directly with the material of construction. In others, the molecular chlorine may react with other compounds to produce species which then react with the material of construction. In the latter instances the corrosion is through the agency of the molecular chlorine.

Compositions comprising 1,2-dichloroethane and a contaminating amount of molecular chlorine originate from a wide variety of sources. A typical source is a reactor system in which ethylene is reacted with molecular chlorine to produce at least one stream of crude 1,2-dichloroethane which comprises 1,2-dichloroethane and a contaminating amount of molecular chlorine and which is introduced to equipment susceptible to corrosion by or through the agency of molecular chlorine. One previous way of reducing the molecular chlorine content of the crude 1,2-dichloroethane stream in an effort to reduce corrosion of the equipment has been to feed excess ethylene to the reactor system. Ethylene present in the resulting stream of crude 1,2-dichloroethane can, given sufficient retention time, react with molecular chlorine to reduce the molecular chlorine content, but the rate of reaction is low. Consequently, equipment of large capacity which will allow a sufficiently long retention time to reduce the molecular chlorine content to an acceptably low level before introducing the stream to the equipment for which corrosion reduction is desired, must be provided.

It has now been found that one or more olefins having a greater reactivity with molecular chlorine than ethylene may be admixed with a composition comprising 1,2-dichloroethane and a contaminating amount of molecular chlorine, and reacted with at least some of the molecular chlorine present. Since the rate of reaction of the reactive olefin and molecular chlorine is greater than that of ethylene and molecular chlorine, the retention time necessary to reduce the molecular chlorine content to a given level is reduced when reactive olefin, in lieu of or in addition to ethylene, is employed as a scavenger for molecular chlorine. When the composition is a moving stream, the capacity of the associated equipment required to provide the necessary retention time is correspondingly reduced. In some cases, the ordinary piping used to convey the stream to the equipment for which corrosion reduction is desired, provides sufficient capacity and retention time. In others, larger or longer piping or a hold-up vessel is necessary, but the capacity of such equipment is considerably less than would be required for ethylene alone.

In most instances where the composition is a stream of crude 1,2-dichloroethane, the stream and reactive olefin are admixed before introduction of the stream to a separation system from which purified 1,2-dichloroethane is removed. However, where for any reason a reduction in corrosion is not desired for the early stages of the separation system (e.g., they are constructed of sufficiently corrosion-resistant material), a fraction of the stream, which fraction comprises 1,2-dichloroethane and a contaminating amount of molecular chlorine, may be admixed with reactive olefin after the early stages and prior to the later stages where corrosion reduction is desired.

In reacting ethylene and molecular chlorine in a reactor system to produce a stream of crude 1,2-dichloroethane, it is desirable to maximize the yield of 1,2-dichloroethane based on ethylene. Introduction of the reactive olefin as additional feed to the reactor system for the purpose of reducing the molecular chlorine content of the effluent is inconsistent with this desired maximization, because the reactive olefin will compete with ethylene for molecular chlorine in the reactor system and, being more reactive, will reduce 1,2-dichloroethane yields. Therefore, the reactive olefin and the crude 1,2-dichloroethane or the fraction thereof should be admixed at some point after the stream of crude 1,2-dichloroethane has left the region of principal ethylene reaction and prior to the equipment for which corrosion reduction is sought.

Accordingly, in the method wherein a composition comprising 1,2-dichloroethane and a contaminating amount of molecular chlorine is introduced to equipment susceptible to corrosion by or through the agency of molecular chlorine, the invention is the improvement comprising: admixing the composition and a scavenging amount of at least one olefin containing at least 7 carbon atoms, and reacting at least a portion of the olefin with at least a portion of the molecular chlorine to reduce the molecular chlorine content of the composition prior to the introduction.

The 1,2-dichloroethane content of the composition with which the reactive olefin is admixed is susceptible to extremely wide variation. Ordinarily the 1,2-dichloroethane content is in the range of from about 90 percent to about 99.99 percent, by weight. Often it is in the range of from about 92 percent to about 99.9 percent by weight. From about 95 percent to about 99.5 percent by weight is preferred.

The molecular chlorine content of the composition with which the reactive olefin is admixed may vary considerably, but in general it is present in a contaminating amount. By a "contaminating amount" is meant a concentration greater than zero but less than about 5000 parts per million, by weight (hereinafter "ppm"). Ordinarily, the molecular chlorine content is in the range of from about 0.1 to about 1000 ppm. Often it is in the range of from about 1 to about 500 ppm.

It is generally easier to separate 1,2-dichloroethane from the products of the reaction between the reactive olefin and molecular chlorine if the normal boiling points of the reactive olefin and its chlorination products are greater than that of 1,2-dichloroethane. For this reason, it is preferred that the reactive olefin contain at least 7 carbon atoms. From about 8 to about 20 carbon atoms is especially preferred.

The reactive olefin may be straight chain, it may be branched, or it may be cyclic. It usually contains one ethylenic double bond, but it may contain more than one such bond. Ordinarily the reactive olefin is unsubstituted, but minor substituents may be attached to the molecule so long as their identities and their numbers do not seriously interfere with the chlorine-scavenging property of the compound. When the reactive olefin is cyclic, the double bonds of the ring should be ethylenic and not aromatic. It is preferred that the reactive olefin be aliphatic and a member of the series $C_nH_{2n+k}$, where the value of n is as discussed above and $k = 2 - 2d$ in which d is the number of ethylenic double bonds in the molecule. Often the value of d is 1 or 2, although it may be greater. Preferably, the value of d is one, and the reactive olefin is a member of the series $C_nH_{2n}$.

Examples of suitable reactive olefins include 1-octene, 1,7-octadiene, cyclooctene, 1,5-cyclooctadiene and 1,5,9-cyclododecatriene. Either a simple reactive olefin or a mixture of reactive olefins may be used as is desired.

The amount of reactive olefin admixed with the composition may vary considerably. In general, it is used in a scavenging amount. By "scavenging amount" is meant that amount which will cause a significant reduction in molecular chlorine content. The molar ratio of the reactive olefin employed to the molecular chlorine present in the composition with which the reactive olefin is admixed, is usually in the range of from about 0.5:1 to about 10:1. Often the molar ratio is in the range of from about 0.9:1 to about 3:1. It is preferred that at least a stoichiometric amount of reactive olefin be used. A molar ratio in the range of from 1:1 to about 10:1 is typical. The preferred molar ratio is in the range of from 1:1 to about 3:1.

The reactive olefin may be in the solid phase, the liquid phase or the vapor phase when it is admixed with the composition. All of the reactive olefin may be in one phase or some may be in one phase and some in another. The composition may be in the liquid phase or the vapor phase during mixing with the reactive olefin. All of the composition may be in one phase or some may be in the liquid phase and some in the vapor phase. The mixing may be accomplished while the composition is stored in a container or while the composition is a moving stream.

The reaction between the reactive olefin and the molecular chlorine may be conducted in the liquid phase, the vapor phase or in both phases. The reaction may be conducted while the mixture is stored in a container or while the mixture is a moving stream.

The temperature at which the reaction between the reactive olefin and molecular chlorine is conducted may vary widely, but it is usually in the range of from about 20° C. to about 150° C. In many cases it is in the range of from about 90° C. to about 130° C. From about 95° C. to about 115° C. is preferred.

The reaction is usually conducted at about ambient atmospheric pressure or a little higher, but greater or lesser pressures may be used. Pressures in the range of from about 0 to about 275 kilopascals, gauge, are generally employed. Pressures in the range of from about 30 to about 120 kilopascals, gauge, are preferred.

In general, the retention time should be sufficient to achieve more than a trivial reduction in molecular chlorine content before the composition is introduced to the equipment for which corrosion reduction is desired.

In the broadest aspects of the invention, the composition with which the relative olefin is admixed may be from substantially any source which provides a contaminating amount of molecular chlorine. Typical sources of the composition include those in which ethylene is reacted with molecular chlorine in the liquid phase, the vapor phase or in both the liquid phase and the vapor phase. See U.S. Pat. Nos. 1,231,123; 2,043,932; 2,099,231; 2,245,776; 2,356,785; 2,393,367 and 2,601,322, the entire disclosures of which are incorporated herein by reference, directed to chlorination in the liquid phase and/or vapor phase. It is preferred that the invention be used in conjunction with a process in which ethylene and molecular chlorine are reacted in the liquid phase. The composition so produced is usually removed from the reactor system in the vapor phase, but it may be removed in the liquid phase. It is especially preferred that the liquid phase chlorination reaction conducted in the presence of ferric chloride; see U.S. Pat. Nos. 2,356,785 and 2,393,367, referenced above.

The equipment susceptible to corrosion by or through the agency of molecular chlorine and for which corrosion reduction is desired, may be substantially any equipment with which the composition comprising 1,2-dichloroethane and a contaminating amount of molecular chlorine ordinarily comes into contact. Usually such equipment is used for storage, transportation, and/or processing. Examples include storage tanks, railway tank cars, tank trucks, piping systems, portions of piping systems, pumps, separation systems, portions of separation systems, condensers, vaporizers, heaters and distillation columns. It is preferred to use the present invention to reduce corrosion in separation systems from which purified 1,2-dichloroethane is removed or to reduce corrosion in portions of such systems. An example of such a separation system is shown in U.S. Pat. No. 2,356,785.

1,2-Dichloroethane is a product of many uses, including use as a solvent and use as feed for the production of vinyl chloride by pyrolysis. The invention is further described in conjunction with the following examples which are to be considered illustrative rather than limiting, and in which all parts are parts by weight and all percentages are percentages by weight unless otherwise specified.

EXAMPLE I

Octene-1 was dissolved in 1,2-dichloroethane. Vaporized mixture of octene-1 and 1,2-dichloroethane was metered into an arm of a first tee and molecular chlorine vapor was metered into a separate arm of the tee. The two streams were thoroughly mixed. The resulting mixture was passed into a second tee containing a thermometer in one leg. The second tee was wrapped with heating tape and insulated. The thermometer controlled a Therm-O-Watch controller which, in turn, activated the heating tape. A tube passed through the wall of the second tee and downward through the interior of the second tee. The tube was terminated with a coarse glass frit which extended below the second tee and into a reducing adapter. The glass frit fit snugly into the narrowest section of the reducing adapter so that all of the mixture of octene-1, 1,2-dichloroethane, and molecular chlorine passed close to the glass frit. A plug of glass wool was placed in the reducing adapter immediately after the glass frit. An insulated 90° adapted was attached to the lower end of the reducing adapter and a water-cooled condenser was attached to the outlet end of the 90° adapter. The entire volume of the reaction space was about 280 milliliters, measured from the molecular chlorine injection point to the end of the outlet joint where the vapor entered the condenser. Nothing was introduced through the glass frit. The molecular chlorine content of the condensate was ascertained by mixing samples of the condensate with aqueous 10% potassium iodide solution and a starch indicator and titrating with aqueous 0.01001N sodium thiosulfate solution. The minimum concentration of molecular chlorine in the condensate which was detectable by this method was about 0.1 to about 0.3 ppm, depending upon sample size. Consequently, the results for low concentrations of molecular chlorine are expressed as "less than" or as "less than or equal to" the reported value. The conditions and results are shown in Table 1.

TABLE 1

Reduction of Molecular Chlorine Content of Mixtures of 1,2-Dichloroethane and Molecular Chlorine Using Octene-1

Conditions

| Temperature: | 110° C. to 120° C. |
| Retention Time: | Approximately 2.8 Seconds |

| Run | $C_8H_{16}:Cl_2$ Molar Ratio | ppm Fed | Molecular Chlorine ppm Found | % Recovery | % Destruction |
| --- | --- | --- | --- | --- | --- |
| 1 | 0 | 46.1 | 35.7 | 77.3 | — |
| 2 | 0 | 45.4 | 39.3 | 86.5 | — |
| 3 | 2.1 | 45.4 | 0.2 | 0.4 | 99.5 |
| 4 | 2.1 | 45.4 | 0.2 | 0.4 | 99.6 |
| 5 | 1.26 | 75.5 | 0.2 | 0.2 | 99.7 |
| 6 | 1.26 | 75.1 | 0.2 | 0.2 | 99.7 |

EXAMPLE II

The apparatus and general procedure of Example I were used to investigate greater amounts of contaminating molecular chlorine when employing octene-1 as a scavenger, and to identify the reaction products. The conditions and results are shown in Table 2.

TABLE 2

Reduction of Molecular Chlorine Content of Mixtures of 1,2-Dichloroethane and Molecular Chlorine Using Octene-1

Conditions

| Temperature: | 110° C. to 117° C. |
| Retention Time: | Approximately 2.8 Seconds |

| Run | $C_8H_{16}:Cl_2$ Molar Ratio | ppm Fed | Molecular Chlorine ppm Found | % Recovery | % Destruction |
| --- | --- | --- | --- | --- | --- |
| 1 | 0 | 2330 | 2160 | 92.8 | — |
| 2 | 0 | 2360 | 2320 | 94.0 | — |
| 3 | 0.98 | 2260 | 0.2 | 0.008 | >99.9 |
| 4 | 0.98 | 2300 | 0.4 | 0.018 | >99.9 |
| 5 | 0.98 | ~2300 | ND[1] | ND | ND |

[1]ND = Not Determined. The purpose of Run 5 was to collect condensate for analysis.

Using gas chromatography and mass spectroscopy, the condensate collected in Run 5 was found to contain a dichlorooctane as a reaction product. It is believed this dichlorooctane was 1,2-dichlorooctane.

Although the present invention has been described with reference to specific details of certain embodiments thereof, it is not intended that such details should be regarded as limitations upon the scope of the invention except insofar as they are included in the accompanying claims.

I claim:

1. In the method wherein a composition comprising 1,2-dichloroethane and a contaminating amount of molecular chlorine is introduced to equipment susceptible to corrosion by or through the agency of molecular chlorine, the improvement comprising: admixing said composition and a scavenging amount of at least one olefin containing at least 7 carbon atoms, and reacting at least a portion of said olefin with at least a portion of said molecular chlorine to reduce the molecular chlorine content of said composition prior to said introduction.

2. The method of claim 1 wherein the molecular chlorine content of said composition with which said olefin is admixed, is in the range of from about 0.1 to about 1000 parts per million by weight.

3. The method of claim 1 wherein the 1,2-dichloroethane content of said composition with which said olefin is admixed, is in the range of from about 90 percent to about 99.99 percent, by weight.

4. The method of claim 1 wherein the molar ratio of said olefin to said molecular chlorine present in said composition with which said olefin is admixed, is in the range of from about 0.5:1 to about 10:1.

5. The method of claim 1 wherein the temperature at which said reaction is conducted, is in the range of from about 20° C. to about 150° C.

6. The method of claim 1 wherein said reaction is conducted in the liquid phase, the vapor phase or in both the liquid phase and the vapor phase.

7. The method of claim 1 wherein said reaction is conducted in the vapor phase.

8. The method of claim 1 wherein said olefin is a member of the series $C_nH_{2n}$ where the value of n is from 8 to about 20.

9. The method of claim 1 wherein said olefin is octene-1.

10. The method of claim 1 wherein said composition is a moving stream.

11. The method of claim 1 wherein said composition is a stream of crude 1,2-dichloroethane.

12. The method of claim 11 wherein said stream has been produced by reacting ethylene with molecular chlorine.

13. The method of claim 11 wherein said equipment is a separation system from which purified 1,2-dichloroethane is removed.

14. In the method wherein:
a. ethylene and molecular chlorine are reacted in the liquid phase in a reactor system to produce 1,2-dichloroethane,
b. at least one stream of crude 1,2-dichloroethane, said stream comprising 1,2-dichloroethane and a contaminating amount of molecular chlorine, is removed from said reactor system in the vapor phase, and
c. said stream is introduced to a separation system from which purified 1,2-dichloroethane is removed, the improvement comprising:
d. admixing said stream and a scavenging amount of at least one olefin containing at least 7 carbon atoms, and
e. reacting at least a portion of said olefin with at least a portion of said molecular chlorine to reduce the molecular chlorine content of said stream prior to said introduction.

15. The method of claim 14 wherein said reaction of ethylene and molecular chlorine is conducted in the presence of ferric chloride.

16. The method of claim 14 wherein said olefin is a member of the series $C_nH_{2n}$ where the value of n is from 8 to about 20.

17. The method of claim 14 wherein said olefin is octene-1.

18. The method of claim 14 wherein the temperature at which said reaction between said olefin and said molecular chlorine is conducted, is in the range of from about 20° C. to about 150° C.

* * * * *